United States Patent
Wang

(10) Patent No.: US 10,076,539 B2
(45) Date of Patent: Sep. 18, 2018

(54) PHARMACEUTICAL USE OF POTASSIUM HYDROXIDE

(71) Applicant: Zhibao Wang, Hefei (CN)

(72) Inventor: Zhibao Wang, Hefei (CN)

(*) Notice: Subject to any disclaimer, the term of this patent is extended or adjusted under 35 U.S.C. 154(b) by 0 days.

(21) Appl. No.: 15/625,300

(22) Filed: Jun. 16, 2017

(65) Prior Publication Data

US 2017/0360827 A1    Dec. 21, 2017

(30) Foreign Application Priority Data

Jun. 17, 2016 (CN) .......................... 2016 1 0451115

(51) Int. Cl.
*A61K 33/00* (2006.01)
*A61K 9/00* (2006.01)
*A61K 9/08* (2006.01)

(52) U.S. Cl.
CPC ............ *A61K 33/00* (2013.01); *A61K 9/0014* (2013.01); *A61K 9/0053* (2013.01); *A61K 9/08* (2013.01)

(58) Field of Classification Search
CPC ......... A61K 9/0014; A61K 33/00; A61K 9/08
See application file for complete search history.

(56) References Cited

U.S. PATENT DOCUMENTS

| | | | |
|---|---|---|---|
| 4,559,315 A * | 12/1985 | Chang | B01J 29/40 502/71 |
| 5,306,511 A * | 4/1994 | Whang | A61K 33/00 426/66 |
| 2011/0262558 A1* | 10/2011 | Huckfeldt | A61K 8/19 424/618 |

OTHER PUBLICATIONS

Al-Hamdi et al (Indian Journal of Dermatology, 2012, vol. 57, pp. 38-41).*
GoutAndYou.com (Gout and Potassium, https://goutandyou.com/gout-and-potassium/, Message Board Postings from Jun. 2014).*

* cited by examiner

*Primary Examiner* — Mark V Stevens
(74) *Attorney, Agent, or Firm* — Novoclaims Patent Services LLC; Mei Lin Wong

(57) ABSTRACT

This relates to the pharmaceutical use of KOH, in forms of topical, oral drugs or intravenous drip, prepared for treating high blood uric acid, especially gout. The external application refers to footbath in soaking solution or embrocation on attack position. The action of the drugs is also to promote the excretion of uric acid. Compared with colchicine and other drugs, KOH has three notable features. First, it takes effect quickly. No matter being applied by footbath, oral or embrocation, it can relieve symptoms within ten minutes, and the pain during gout attack will be significantly reduced. Second, it takes curative effect quickly. After application of the drugs for 2-3 consecutive days, gout symptoms will completely disappear. Third, it has no side effects. In one respect, with a low concentration, the KOH will not corrode the skin. In a further respect, potassium ion itself is diuretic and it has no harm to kidney.

3 Claims, No Drawings

PHARMACEUTICAL USE OF POTASSIUM HYDROXIDE

1. TECHNICAL FIELD

This invention relates to the new uses of a known compound, to speak specifically, it is a pharmaceutical application of potassium hydroxide (KOH).

2. BACKGROUND OF THE INVENTION

At present, high blood uric acid is a direct or indirect risk factor of the diseases harmful to human health, such as gout, urinary calculi, renal disorder, obesity, hypertension, hyperlipemia, diabetic arteriosclerosis, cardiovascular disease, cerebrovascular disease and chronic nephritis. Urate is easy to deposit in endocardium, epicardium and cardiac valves, and further causing the abnormal phenomenon of cardiac damage, arrhythmia, cardiac insufficiency et al. It is found from the clinical observation of 6,403 patients that blood uric acid level is an independent risk factor for renal dysfunction (*The Diagnosis and Treatment of Gout*, written by Zhao Shengchuan in pages 40-47, published by Military Medical Science Press in February 2002). According to the statistics of International Health Organization, high blood uric acid sufferers live six years less on average than healthy people. According to 2015 Gout Classification Criteria: An American College of Rheumatology/European League Against Rheumatism Collaborative Initiative, the incidence of gout in the United States is 3.9%, in France is 0.9%, the United Kingdom 1.4%-2.5%, Germany 1.4%, New Zealand European and Maori 3.2% and 6.1 respectively. In China, the number of patients who die from the disease associated with high blood uric acid is up to more than three million each year, and the patients outnumber 500 million. To lower the level of high blood uric acid is the basis for the treatment of these diseases.

Uric acid is a heterocyclic compound containing carbon, hydrogen, nitrogen and oxygen, and a metabolite of purine. Its scientific name is 2,6,8-Trihydroxypurine, molecular formula is $C_5H_4N_4O_3$, molecular weight is 168.10, symbol is HUr, and its dissociation constants (PKa) are 5.75 (the $9^{th}$ nitrogen dissociation) and 10.3 (the $3^{rd}$ nitrogen dissociation) respectively. It is a white crystal. Its melting point >300° C. It is slightly soluble in boiling water and well soluble in alkali. The solubility with sodium urate solution at 37° C. is 8.0 mmol/L, and the solubility with uric acid at 37° C. is 0.5 mmol/L. Its solubility product constant Ksp is respectively as follows:

$$Ksp(\text{sodium urate}) = (Na^+)(Ur^-) = 0.008 \times 0.008 = 6.4 \times 10^{-5}$$

$$Ksp(\text{uric acid}) = (H^+)(Ur^-) = 0.0005 \times 0.0005 = 2.5 \times 10^{-7}$$

There is certain amount of uric acid contained in the body of healthy people. In addition, the body generates some new uric acid and discharges some uric acid for an amount equivalent to the generated amount every day in order to maintain balance. Once the balance is broken, the excess uric acid in vivo will lead to high blood uric acid, which is the main cause of gout. However, there are such a small number of gout patients that their determination of blood uric acid is normal when gout attacks just because of the precipitation of uric acid crystals. The case of elevated blood uric acid without gout attack is usually named as high blood uric acid.

At present, there are two major categories of drugs to lower blood uric acid and treat gout, that is, inhibit the synthesis of uric acid and accelerate the excretion of uric acid in vivo. Allopurinol Tablet is used to inhibit the synthesis of uric acid in vivo. The drugs used to promote urate excretion mainly include Sodium Bicarbonate, Colchicine, Probenecid, Anturane and Benzbromarone. However, no matter what medicine to use, corresponding side effects and contraindications will be generated. For example, colchicine can lower uric acid, but it will cause renal failure. Therefore, it is an urgent problem to be solved worldwide to develop safe, effective and quick blood uric acid lowering drugs.

The invention is originated from a patent applicant who had high blood uric acid and ultimately caused gout. In the physical examination in 1980, an excessive amount of blood uric acid was found from his body, but that did not attract his attention. The signs of gout appeared in 2006. Gout attacked him in 2008 and then he was unable to walk. Having been persistently exploring for eight years, no matter topical drugs or oral drugs, he tried all the drugs in person, and also allowed his gout wardmates who agreed to try the drugs to participate in the attempts. As the saying goes that he who repeatedly breaks arm eventually becomes an experienced doctor. Upon the practice of "repeatedly breaking arm", the applicant finally found out the pharmaceutical use of KOH in lowering blood uric acid and treating gout.

3. SUMMARY OF THE INVENTION

This invention is aimed to provide a therapeutic medicine for patients with high blood uric acid, especially gout. The technical problem to be solved is to effectively lower the content of uric acid in blood.

The medical application of KOH refers to the application of KOH in the preparation of medicine for treating high blood uric acid, especially gout.

It is found after attempts personally, the effective application of the foresaid drugs is by means of topical and oral uses.

The patients with high blood uric acid should use the KOH solution to soak feet (i.e. footbath). Water is used as solvent to prepare a solution with the concentration of 0.01-0.05 mol/L(KOH), that is, the soaking solution, used directly for footbath. The solution can be also heated to 40-48° C. and then used for footbath. For acute gout attack, if the attack position is easy to soak, such as ankles, toe joints, hands and wrist joints, the solution can also be used to soak such positions. The solution should be embrocated on the attack positions if such positions are not convenient to soak, such as knee joints and elbow joints. Water is used as solvent to prepare a solution with the concentration of 0.01-0.05 mol/L(KOH), that is, the embrocation. Drip a cotton swab in the embrocation and embrocate on the attack positions, or drip a dressing in the embrocation and apply on the attack positions. It is very inconvenient to undress when applying topical drug in cold season, then oral drug is an option. Water is used as solvent to prepare a solution with the concentration of 0.001 mol/l-0.005 mol/l (KOH), that is, the oral liquid. Have 50 ml of the liquid before meals. For the sufferers of high blood uric acid and acute, intermittent and chronic gout, the embrocation, soak solution and oral liquid can be used separately or concurrently at the same time.

The action of the topical drugs and the oral drugs of KOH is also to promote the excretion of uric acid. Compared with colchicine and other drugs, KOH has three notable features. First, it takes effect quickly. No matter being applied by footbath, oral or embrocation, it can relieve symptoms within ten minutes, that is, the pain and swelling during gout attack will be significantly reduced, and those cannot walk can walk basically. Second, it takes curative effect quickly. After application of the drug for 2-3 consecutive days, gout symptoms will completely disappear and everything get back to normal. Third, it has no side effects. In one respect, with a low concentration, the KOH will not corrode the skin. In a further respect, potassium ion itself is diuretic, with no harm to kidney.

With Such Effects, KOH Works in the Principle Below:

The uric acid exists in blood mainly in the form of sodium urate (NaUr), and few in the form of uric acid molecule (HUr). If uric acid level in blood rises, and when the concentration of uric acid and sodium urate rise to respective ion product greater than e solubility product constant, uric acid and sodium urate will crystallize and separate out. Gout is just caused by the separated crystals settled in the positions of joints. Other diseases will be caused if the separate crystals settle in other positions.

Because of the permeability of blood vessels, after being absorbed through skin, KOH penetrates into blood and reacts chemically as follows:

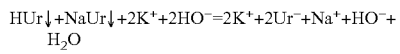

$$HUr\downarrow + NaUr\downarrow + 2K^+ + 2HO^- = 2K^+ + 2Ur^- + Na^+ + HO^- + H_2O$$

KOH takes neutralization reaction with uric acid and takes ion exchange reaction with sodium urate, and both generate potassium urate. The solubility of potassium urate is much higher than uric acid and sodium urate, which can gradually dissolve the precipitated crystals, and gout symptoms are hereby relieved. When all the precipitated crystals are dissolved, the gout symptoms will completely disappear. Meanwhile, the formation of uric acid potassium is more conducive to uric acid excretion from the urine, and the content of uric acid in blood is lowered accordingly. In addition, the fluid and urine of high blood uric acid sufferers tend to be acidic. Potassium urate is the salt produced by the reaction of weak acid and strong alkali, and it is alkaline after hydrolysis in solution. Therefore, KOH is good for high blood uric acid sufferers to improve their physique.

Based on the above theory and the practice of the applicant, it is anticipated that if KOH will have an immediate effect to high uric acid and gout sufferers if it can be processed into water injection for intravenous drip. In view of human vascular tolerance of pH is 4-9, the concentration of the drip is better to be 1-10 can be mol/L.

IV. EMBODIMENT (i) Preparation of Topical Drugs

1. Preparation of Soaking Solution

Take KOH 0.56 kg, dissolve in 1 liters of distilled water, and get a concentration of 0.01 mol/L.

2. Preparation of Embrocation

Take KOH16.8 g, dissolve in 1 liters of distilled water, and get a concentration of 0.3 mol/L.

2. Preparation of Oral Liquid

Take KOH0.12 g, dissolve in 1 liters of distilled water, and get a concentration of 0.0021 mol/L. Take orally for 50 ml per time and one time per day.

The aforesaid KOH is a solid body. Add in chemical pure reagent when used externally, and add analytical reagent when used orally.

(ii) Experiments in Lowering Blood Uric Acid and Curing Gout

The applicant tried the drugs in person

In May 2008 when the applicant had gout attack at the position of the first metatarsophalangeal joint, his foot could not touch the ground. He dripped a cotton swab into the embrocation (0.1 mol/L) prepared by himself and embrocated on the attack position. In about ten minutes, the pain was relived and his foot could be able to touch the ground. He kept embrocating for 2-3 times per day, and gout symptoms disappeared three days later and everything got back normal.

Since then, the applicant had gout attack once a year and even twice or three times when being severe. The time is uncertain, but the position is always on foot. It is the forerunner of gout that the foot got swollen with soreness. From 2009, once he noticed the forerunner of gout, he immediately embrocated KOH solution, and the swelling and soreness disappeared quickly, which effective prevented the onset of gout. During a period of five years till 2013, the molar concentration of KOH solution of 0.1, 0.2, 0.3 and 0.4 was used respectively, and all were effective. The higher molar concentration was, the more obvious effect was.

KOH embrocation can relieve gout symptoms and cure gout through promoting uric acid excretion and lowering blood uric acid. However, this is qualitative. In order to get the quantitative data of lowering blood uric acid, he began to take footbath with KOH soaking solution, and then went to the doctor to test blood uric acid immediately.

2. Footbath in KOH Soaking Solution

The blood uric acid tested on Dec. 2, 2014 was 455 μmol/L. In order to take the test, he was requested to eat two chicken livers that day. The next day the tested blood uric acid is 495 μmol/L, and the urine uric acid tested was 6.3 mmol/L, which showed that exogenous purine supplementation could increase the level of blood uric acid. On December 3, he took a footbath in 45° C. soaking solution (0.01 mol/L) for an hour, and then went to test at Chaohu Hospital of Anhui Medical University. The tested blood uric acid was 486 μmol/LL, and the urine uric acid tested was 6.59 mmol/L. The blood uric acid was lowered and the urine uric acid was increased, which showed that the footbath had effectively promoted the excretion of uric acid. He kept taking footbath for once a day, on December 10, the tested blood uric acid was 389 μmol/L, dropping by 21%, and had dropped to the range of normal value, 208-428 μmol/L.

3. Test with Oral Liquid

After many years of practice in external application, the applicant realized that KOH alkaline strong though, it would have no harm to human body as long as its concentration is appropriately controlled, with no harm to skin and no harm to digestive tract. Besides, the absorption through digestive tract must be faster than percutaneous absorption, and is very convenient. So he began to take oral use tests from January 2016. To April 2016, the applicant had taken KOH solution for 23 times in order to get the ideal concentration. The oral concentration (mol/L) he had tried includes 0.001, 0.0018, 0.0021, 0.0025, 0.003, 0.005 and 0.008 in turn. At last, the concentration of oral liquid was determined to be 0.001 mol/L-0.005 mol/L. With such concentration, the oral liquid tasted same as boiled water, and brought no discomfort to the body.

Tested at Philip Ts, Chaohu City, Anhui Medical Devices Co., Ltd. on a day in April 2016, blood uric acid was 351 μmol/L, which was lowest value so far.

Test of 8 Gout Sufferers

Tested blood uric acid on Apr. 18, 2015, and took footbath in 45° C. soaking solution (0.01 mol/L) for an hour that day, and once a day later and lasted for three days. Tested blood uric acid on April 21 again. The data was summarized as follow:

| Name | Gender | Age | BUA bf Bath µmol/L | BUA af Bath µmol/L | Drop by % |
|---|---|---|---|---|---|
| Yu Wenjun | M | 58 | 796 | 566 | −28.8% |
| Fang Yuanping | M | 63 | 620 | 566 | −8.7% |
| Xiang Songbai | M | 74 | 499 | 474 | −5.0% |
| Ye Mingru | M | 66 | 459 | 423 | −7.8% |
| Hu Chunrong | M | 47 | 476 | 500 | +5% |
| Xu Wenming | F | 53 | 376 | 509 | +35% |
| Jiang Ping | M | 68 | 451 | 512 | +13.5% |
| Zhang Xianfu | M | 67 | 706 | 618 | −12.5% |

The patient Xu Wenmei was tested at Anhui Chaohu Orthopedic Hospital before the bath and at Anhui Chaohu Ethnics Hospital (Dongfeng Community Health Service Station) after the bath.

The patient Jiang Ping was tested at The Eighth People's Hospital of Hefei before and after the bath.

The patient Zhang Xianfu was tested at Chaohu Hospital of Anhui Medical University before and after the bath.

The other five patients were tested at Anhui Chaohu Orthopedic Hospital before and after the bath.

The blood uric acid of the three patients Hu Chunrong, Xu Wenmei and Jiangping wsa increased because they were going through gout attack during that period. The blood uric acid was crystallized and separated out. The crystals dissolved after the bath, which caused the increase of blood uric acid.

What is claimed is:

1. A method of lowering blood uric acid in a human subject for gout treatment comprising the step of: administering a drug composition of potassium hydroxide to the human subject, wherein the drug composition is a soaking solution for external use and the potassium hydroxide has a concentration of 0.01-0.05 mol/L.

2. A method of lowering blood uric acid in a human subject for gout treatment comprising the step of: administering a drug composition of potassium hydroxide to the human subject, wherein the drug composition is an embrocation for external use and the potassium hydroxide has a concentration of 0.1-0.5 mol/L.

3. A method of lowering blood uric acid in a human subject for gout treatment comprising the step of: administering a drug composition of potassium hydroxide to the human subject, wherein the drug composition is an injection solution and the potassium hydroxide has a concentration of 1-10 µmol/L.

* * * * *